United States Patent
Monteiro

(12) 
(10) Patent No.: US 11,504,016 B1
(45) Date of Patent: Nov. 22, 2022

(54) METHOD AND MEANS TO MEASURE HEART RATE WITH FITBIT DEVICES—2

(71) Applicant: Sergio Lara Pereira Monteiro, Los Angeles, CA (US)

(72) Inventor: Sergio Lara Pereira Monteiro, Los Angeles, CA (US)

( * ) Notice: Subject to any disclaimer, the term of this patent is extended or adjusted under 35 U.S.C. 154(b) by 0 days.

(21) Appl. No.: 17/492,655

(22) Filed: Oct. 3, 2021

Related U.S. Application Data

(62) Division of application No. 17/113,035, filed on Dec. 5, 2020, now Pat. No. 11,172,836.

(60) Provisional application No. 62/944,293, filed on Dec. 5, 2019.

(51) Int. Cl.
*A61B 5/024* (2006.01)
*A61B 5/00* (2006.01)
*A61B 5/11* (2006.01)

(52) U.S. Cl.
CPC ............ *A61B 5/02416* (2013.01); *A61B 5/11* (2013.01); *A61B 5/683* (2013.01)

(58) Field of Classification Search
CPC .... A61B 5/02416–02438; A61B 5/681; A61B 5/026–0261; A61B 5/0295
See application file for complete search history.

(56) References Cited

U.S. PATENT DOCUMENTS

| | | | | |
|---|---|---|---|---|
| 6,188,391 B1 * | 2/2001 | Seely | ................... | G06F 3/0443 345/173 |
| 7,676,253 B2 * | 3/2010 | Raridan, Jr. | ......... | A61B 5/6826 600/344 |
| 8,346,328 B2 * | 1/2013 | Mannheimer | ...... | A61B 5/02416 600/310 |
| 9,445,733 B2 * | 9/2016 | Tanaka | ................... | A61B 5/681 |
| 10,178,959 B1 * | 1/2019 | Homyk | ................ | A61B 5/6824 |
| 10,206,589 B2 * | 2/2019 | Walker | ..................... | A61B 5/11 |
| 10,335,088 B2 * | 7/2019 | Park | ....................... | A61B 5/6843 |
| 10,398,364 B2 * | 9/2019 | Cheng | ................ | A61B 5/02433 |
| 10,568,525 B1 * | 2/2020 | Wu | ....................... | A61B 5/0205 |
| 10,667,704 B2 * | 6/2020 | De Haan | .............. | A61B 5/7207 |
| 10,687,717 B1 * | 6/2020 | Peterson | ................ | A61B 5/681 |
| 10,687,718 B2 * | 6/2020 | Allee | ....................... | A61B 5/11 |
| 10,881,310 B2 * | 1/2021 | Giovangrandi | ........ | A61B 5/721 |
| 2007/0073117 A1 * | 3/2007 | Raridan, Jr. | ........ | A61B 5/14552 600/310 |
| 2008/0004510 A1 * | 1/2008 | Tanzawa | .................. | A61B 5/00 600/301 |
| 2008/0039729 A1 * | 2/2008 | Cho | .................... | A61B 5/02416 600/473 |
| 2009/0054751 A1 * | 2/2009 | Babashan | .......... | A61B 5/14552 600/324 |
| 2009/0112071 A1 * | 4/2009 | LeBoeuf | ................ | A61B 5/721 600/301 |
| 2010/0286494 A1 * | 11/2010 | Addison | .............. | A61B 5/1455 600/310 |
| 2013/0053654 A1 * | 2/2013 | Caduff | .................. | A61B 5/1455 600/301 |

(Continued)

*Primary Examiner* — Oommen Jacob

(57) ABSTRACT

A device and a means to measure the periodic change in blood supply volume, from which the heart rate can be inferred. The device is useful for equipment intended to track the physical activity of animals, including humans, particularly if they are engaging in some sort of physical activity designed to improve the physical performance of the animal. One possible application is to improve the accuracy of the fitbit devices used by dark skinned humans.

16 Claims, 15 Drawing Sheets

(56) References Cited

U.S. PATENT DOCUMENTS

| | | | |
|---|---|---|---|
| 2014/0058217 A1* | 2/2014 | Giovangrandi | A61B 5/14552 600/301 |
| 2014/0107493 A1* | 4/2014 | Yuen | A61B 5/6898 600/473 |
| 2014/0121471 A1* | 5/2014 | Walker | A61B 5/11 600/301 |
| 2014/0135631 A1* | 5/2014 | Brumback | A61B 5/11 600/479 |
| 2014/0142403 A1* | 5/2014 | Brumback | A61B 5/02427 600/324 |
| 2014/0275852 A1* | 9/2014 | Hong | A61B 5/1118 600/301 |
| 2014/0275888 A1* | 9/2014 | Wegerich | A61B 5/6815 600/324 |
| 2015/0148632 A1* | 5/2015 | Benaron | A61B 5/14552 600/322 |
| 2015/0148633 A1* | 5/2015 | Park | A61B 5/0004 600/323 |
| 2015/0216425 A1* | 8/2015 | Gladshtein | A61B 8/0891 600/431 |
| 2016/0007916 A1* | 1/2016 | Iwawaki | A61B 5/0205 600/301 |
| 2016/0058367 A1* | 3/2016 | Raghuram | A61B 5/7278 600/479 |
| 2016/0198962 A1* | 7/2016 | Park | A61B 5/0295 600/480 |
| 2016/0242659 A1* | 8/2016 | Yamashita | A61B 5/7217 |
| 2017/0007138 A1* | 1/2017 | Kim | A61B 5/021 |
| 2017/0011210 A1* | 1/2017 | Cheong | H04W 4/00 |
| 2017/0071518 A1* | 3/2017 | Xavier Da Silveira | A61B 5/14552 |
| 2017/0164848 A1* | 6/2017 | Nadeau | A61B 5/083 |
| 2017/0202466 A1* | 7/2017 | Paulussen | A61B 5/02427 |
| 2017/0224236 A1* | 8/2017 | Ho | A61B 5/0205 |
| 2017/0358723 A1* | 12/2017 | Horikawa | H01L 33/20 |
| 2018/0042513 A1* | 2/2018 | Connor | G06K 9/22 |
| 2018/0049657 A1* | 2/2018 | Paulussen | A61B 5/02427 |
| 2018/0235483 A1* | 8/2018 | Mouradian | G04G 21/00 |
| 2019/0387972 A1* | 12/2019 | Hu | A61B 5/0059 |
| 2020/0367816 A1* | 11/2020 | Panneer Selvam | A61B 5/1455 |

* cited by examiner

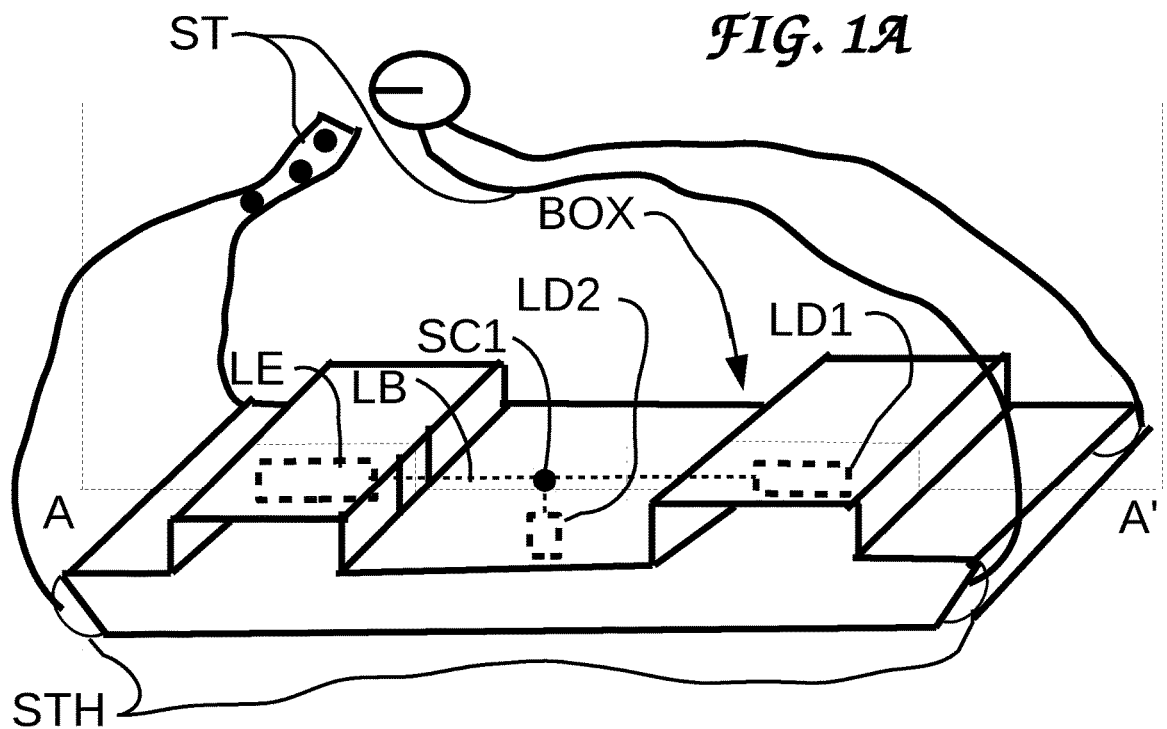
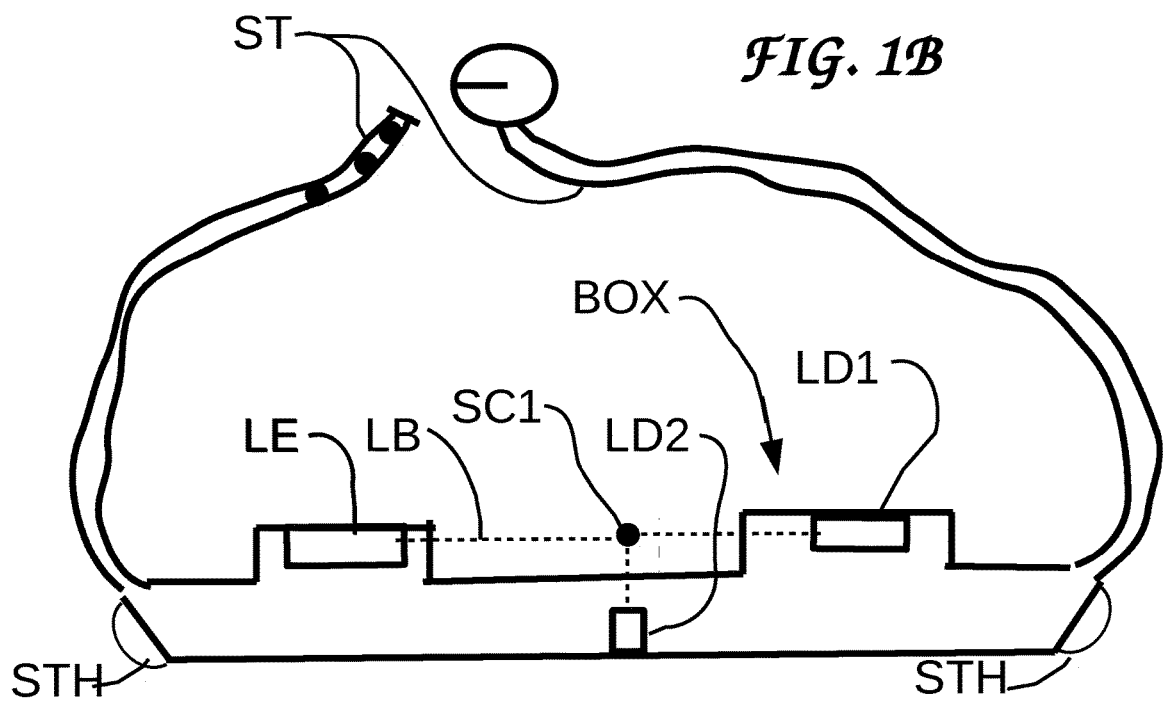

Old art

METHOD AND MEANS TO MEASURE HEART RATE WITH FITBIT DEVICES—2

CROSS-REFERENCE TO RELATED APPLICATIONS

This patent application is a divisional application from patent application Ser. No. 17/113,035, filing date 2020 Dec. 5, currently allowed. This patent application claims priority over the U.S. provisional patent application No. 62/944,293, dated 2019 Dec. 5. This patent application is related to U.S. patent application Ser. No. 16/931,407, dated 2020 Jul. 16.

FEDERALLY SPONSORED RESEARCH

Not applicable

SEQUENCE LISTING OR PROGRAM

Not applicable

BACKGROUND OF THE INVENTION—Field of Invention

This invention relates to fitbit-type devices, specifically to an improved method and means to measure heart rates of the wearer, and in particular to improve the reliability of the heart rate data acquisition when the wearer is of a darker skin complexion.

BACKGROUND—Discussion of Prior Art

For better accuracy and to comply with the USPTO rules, in particular with 35 U.S.C. 112(a) or 35 U.S.C. 112 (pre-AIA), first paragraph, which requires the specification to be written in "full, clear, concise, and exact terms." also requires that the specification be "clear and full" and the use of "exact terms to enable any person skilled in the art or science to which the invention pertains to make and use the same", we want to first define a few of the key terms used in the sequel.

Fitbit—this is a trade name and the name of a company based in San Francisco, but currently used as a noun for any of the "activity trackers, wireless-enabled wearable technology devices that measure data such as the number of steps walked, heart rate, quality of sleep, steps climbed, and other personal metrics involved in fitness" (copied from the fitbit article at Wikipedia, accessed on 2019 Aug. 8). We use the word here in this patent application document as a noun, referring to any device that collects data for physical activity in general, and of the heart rates in particular. In any instance that we intend to refer to the company we will make it explicit, otherwise fitbit here is a noun. As a noun, fitbit means any fitness measurement device, usually wore at the wrist, as a wrist-watch of the fore, which could include a wrist-watch too, which is capable of measure and perhaps also store in computer memory, data related to the physical activity of the wearer.

Normalization. In mathematics the expression "to normalize" refers to the mathematical procedure of modifying a fraction to an equivalent fraction with a standard (or normal) denominator. It may also mean to describe the quantity based on a standard unit (as meters, or millimeter, or inches, etc.). It often means to multiply all the measurements by the same number, in such a way that the highest number, or value, is some chosen value, most often 1 (one). Probabilities, for example, are normalized to 1, because the highest value for them is 1, by convention.

We discuss here the heart beating measurement capability of the fitbits. Our invention is an improvement on the heart rate measurement capability of the fitbits.

Existing fitbit-type devices are well known to fail miserably to make any acceptable measurement the heart rate of darker skinned people—brown and black. This is well documented in the literature, it being easy to find plenty of documented shortcomings for the measurement of the heart rate on darker-skined people, if one just googles any of the terms related to it, e.g. "fitbit heart rate darker skin". Such web search easily find a large number of complaints from darker skinned people, who consistently report that their fitbit-type devices make terribly wrong measurements of their heart rate, wrong when compared with the old-fashioned method of measuring the beats at the pulse with a finger pressed on the wrist and counting the beats for a known length of time. In fact, it is reported that the fitbit heart rates of darker skinned people is sometimes as low as 20 or 30, which is an obviously wrong number if the individual in question is not fainting. This failure of the fitbit-type devices is so well known that it has been measured and published in fitness magazines and published by established university research teams in science journals as well.

Before we proceed, let us add a few words of how the heart beat is measured by the fitbits. It uses a process known in physics as light spectroscopy, which is the process of measuring the light energy that is either absorbed or scattered by a particular molecule. Measuring either scattering or absorption of some molecule present in blood, for example, while not present in other human tissues, gives information about the amount of blood in the volume illuminated by the light—because blood and only blood can cause the change, in such a situation. In this case, where the objective is the determination of the heart beating of the wearer of the fitbit, another feature is also used, that with each heart contraction (systole), the amount of blood in the arteries increases, decreasing after, as the blood continues to fill the veins and be recollected by the heart, (diastole). In short, the fitbit measures the amount of blood at a particular place on the body of the wearer, which, in turn, increases and decreases as the heart pumps the blood. If this can be measured, it follows that each cycle corresponds to a single heart beat. To advance the conclusion later, the problem with the existing fitbit is that they are poor at measuring the blood amount when the fitbit wearer has darker skin, because the melanin absorbs the light, so there is no light inside the body to measure anything!

It is interesting to notice here that spectroscopy is used by our brains to make sense of the world as well, it being how we detect that a leaf is a leaf, that a person is white, brown or black, or that there is a wall ahead of us, so we better not proceed ahead. This is so because part of the information used by our brain is the color of the light scattered towards our eyes: green for light reflected by the leaves, yellow for the light reflected by the hair of a blond person, etc.

The fitbits use the same method. In this case the device is fitted with a light of a particular color, usually green, which is turned on from the base of the device, into the wrist of the wearer, and a green light detector that measures the light reflected back onto the fitbit. The only difference between the fitbits and our eyes being that our eyes are incapable of emit light, so they use the light emitted by the sun, or else the light reflected by the wall of a room we happen to be in, while the fitbit produces it own light, but this is a trivial difference that does not change the nature of the process. It is because the fitbit measures the back-scattered light that the method to measure the heart beating rate is called spectroscopy. Depending on the molecule used by a particular fitbit, there will be a certain fraction of the light that is back-scattered onto the fitbit, which is, in turn, a function of how many of these molecules are in the light path. The measurement is then based on the fact that the amount of blood in the blood vessels change during the heart beating process: more blood at the pressure peak (systole), when the blood is pushed hard into the arteries, less blood at the low part of the cycle (diastole), when the blood flows away from the vessels. So, when there is more blood, there is more of the particular molecule that is measured, and consequently more light back-scattered. In such a situation, the computer in the fitbit is looking for how many times per minute the light intensity goes up and down, then up again and down again, etc., each cycle corresponding to a systole-diastole cycle, which, in turn, corresponds to a heart beat, so measuring the number of cycles, the fitbit is measuring the heart beats. This works as long as there is enough photons (or particles of light) to make each measurement. If, because of melanin absorption for example, the number of photons is too small, then the detection of the maximum-minimum becomes uncertain, and with this so does the number of heart beatings.

Now for the case of our interest here, It is generally accepted that the error of the heart rate reading for darker skinned people, when compared with the same measurement, by the same device, on lighter skinned persons, is due to the use of green light, which is more absorbed by the extra melanin on the skin of the darker skinned individuals, when compared with the less melanin on the skin of the lighter skinned individuals. This green light is used to acquire the data but it hardly penetrates beyond the skin of a dark-skinned person, which is composed of dead cells, being therefore unable to reach the blood underneath the skin, to allow for the measurement of the required data, in this case, the green light intensity that is back-scattered (that is reflected backwards, in non-technical language).

To understand the failure, one needs to look at the measurement process used by the devices. In most existing fitbits, the measurement of the heart beat is made using a green light beam, which is sent into the body of a person, usually the wrist, then measuring the intensity of the light back-scattered (reflected back, in ordinary language). Leaving aside the details, the fitbit process works similarly to the way our brain uses to detect the presence of blood on a wound or skin cut, or a subset of the information used by our brain: a measurement of the back-scattered light intensity of the color red. It stands to reason that for this to work it is necessary that the probing device (the green light) must be able to reach the blood to be measured. It is known that blood absorbs more red and infrared (IR) light than flesh does, and also scatters more red and infrared (IR) light than flesh does, including back-scattering. This differential optical property between blood and flesh can be used to measure the variation of blood that accompanies each and every heart beat. Here we want to highlight the use of a technical term that is easy to understand by a physicist but may be misunderstood by someone with less acquaintance with scientific use of words. When a physicist writes, as I did, "This differential optical property . . . " we mean "the existence of this difference on the optical property . . . ", and also by "optical property" we physicists include at least infrared and ultraviolet with the optical properties, if not beyond these too. It is also worth to point out here, that though the existing fitbits are better at measuring the heart rate of fair skinned people, when compared with darker skinned people, the heart rate measurement even for the fairer skinned people leaves a lot to be desired; in other words, the fitbits do a better job to measure the heart rate for fair skinned people but they still leave a lot to be desired even for the fair skinned people.

This failure of the fitbit devices to correctly measure the heart bit rate on darker skinned people is said to be a consequence of the devices using green light to measure the amount of blood at the wrist, which blood supply increases and decreases just below the skin at the wrist, with each heart beat, and with each in-between beat, respectively. The reason that the fitbits fail for darker skinned people is because darker skinned people have more melanin on their skins, which absorbs enough green light that there are not enough of it to make a measurement, so the fitbits fail for darker skinned people.

On the other hand, it is well known that infrared radiation is capable of penetrating deeper into tissues, including melanin, a point that has been pointed out to the fitbits manufacturers. These manufacturers, in turn, reply that they cannot use red/infrared, instead of green, because of the higher price of the red and/or infrared sources. The inventor knows well that this larger price of the green LED and/or lasers is not true, and so do most of people familiar with the subject. This then brings to the fore the question: what is then the reason to use green light? The true reason is that it is better to measure changes of blood irrigation (blood supply) just under the skin, as opposed to measure changes of blood supply deeper below the skin. Of course that this, in turn, poses another question: why are the fitbit manufacturers lying? The inventors believe that the fitbit manufacturers are holding as a trade secret, instead of making it public and patenting it, the crucial information that what matters most is the change of superficial blood supply, as opposed to deeper blood supply. Though this is the conclusion of the inventor, this particular observation should not be held against the patent application, because the method and means disclosed in this patent application do not depend on the going-ons inside the manufacturers of fitbits, or on the theoretical explanations of the device, but only that the method and means work, as measured by the inventor.

Objects and Advantages

It is one of the objects and advantages of this invention to provide an improved measurement of the heart rate as measured by fitbit-type devices when the wearer of the fitbit-type device is of a darker skin color.

It is another object and advantage of this invention to provide an improved measurement of the heart rate as measured by fitbit-type devices even when the wearer of the fitbit-type device is of a lighter skin color.

It is another object and advantage of this invention to bring some dough to the inventor.

If one or more of the cited objectives is not achieved in a particular case, any one of the remaining objectives should be considered enough for the patent disclosure to stand, as these objectives are independent of each other.

SUMMARY OF THE INVENTION

Our invention discloses the use of infrared radiation, which can penetrate the melanin better than green radiation does, and ALSO directs the infrared radiation to a path parallel to and just under the skin, which prevents deep penetration of the infra-red, because there is more variation of blood supply just below the skin than deep below the skin. Our beautiful invention that will revolutionize the capability of the fitbits to correctly measure the heart rate of the wearer, discloses the use of a light beam propagating just below the skin surface, at a direction substantially parallel to the skin surface to measure the blood volume. Forcing the radiation probing beam (infrared in the main embodiment) to be just under the skin, the device of this invention forces that the measurement occurs at the place where there is larger volume of blood variation, therefore maximizing the resultant measurement. The light used should preferentially be either deep red or infrared, and the beam should preferentially be a collimated beam, as a laser beam, but these are not necessary for the invention to work, but only to work better.

This invention also discloses the collimator that rejects "light" beams that propagate toward the detector along directions not intended to be measured, as, for example, to eliminate scattered photons before they reach and are detected by the "light" detector that is intended to measure the "transmitted" photons, which are the photons that have propagated along the original directions without suffering any scattering event—as per MY DEFINITION of the term, which is my definition used here for convenience and not any usual or accepted terminology. Indeed, without such a collimator many photons would reach the detector that is measuring the "transmitted" radiation that are not "transmitted" photons, but rather are scattered photons propagating toward the detector positioned to measure the "transmitted" radiation but that do propagate along the initial direction of propagation, or, in other words, that are not directly along the initial direction of propagation.

BRIEF DESCRIPTION OF THE DRAWINGS

FIG. 1A. is a perspective view of our invention.

FIG. 1B. is a cross section on the perspective view seen at FIG. 1A at the vertical plane A-A'.

DRAWINGS—List of Reference Numerals

Brief Description of Labels

BOX=holding box or container, which contains the elements of our invention.

infrared (IR)=infrared radiation (IRR). We are using the term as it is understood in physics, all radiation characterized by wavelengths longer than deep red, beyond the visible spectrum. This is how Wikipedia defines it, as assessed on 2020 Nov. 29:
Infrared—Wikipedia
en.wikipedia.org>wiki>Infrared
Infrared (IR), sometimes called infrared light, is electromagnetic radiation (EMR) with wavelengths longer than those of visible light.
LB=Light (radiation) Beam
LD=Light (radiation) detector
LE=Light (radiation) Emitter
radiation=we are using this term as it is used in physics, a short for electromagnetic radiation (EMR), which has nothing to do with cancer causing radiation, as it is assumed by most people. Don't be afraid of radiation here guys, this is physics radiation.
RFitBit=Re-entrance on FitBit,
SFitBit=Surface of FitBit
SC1=scattering center 1
SF=surface
SK=skin
SP=SC=Scattering point or scattering center
ST=strap
STH=strap holder
WIN=window, optical window

DETAILED DESCRIPTION

Figure 7:
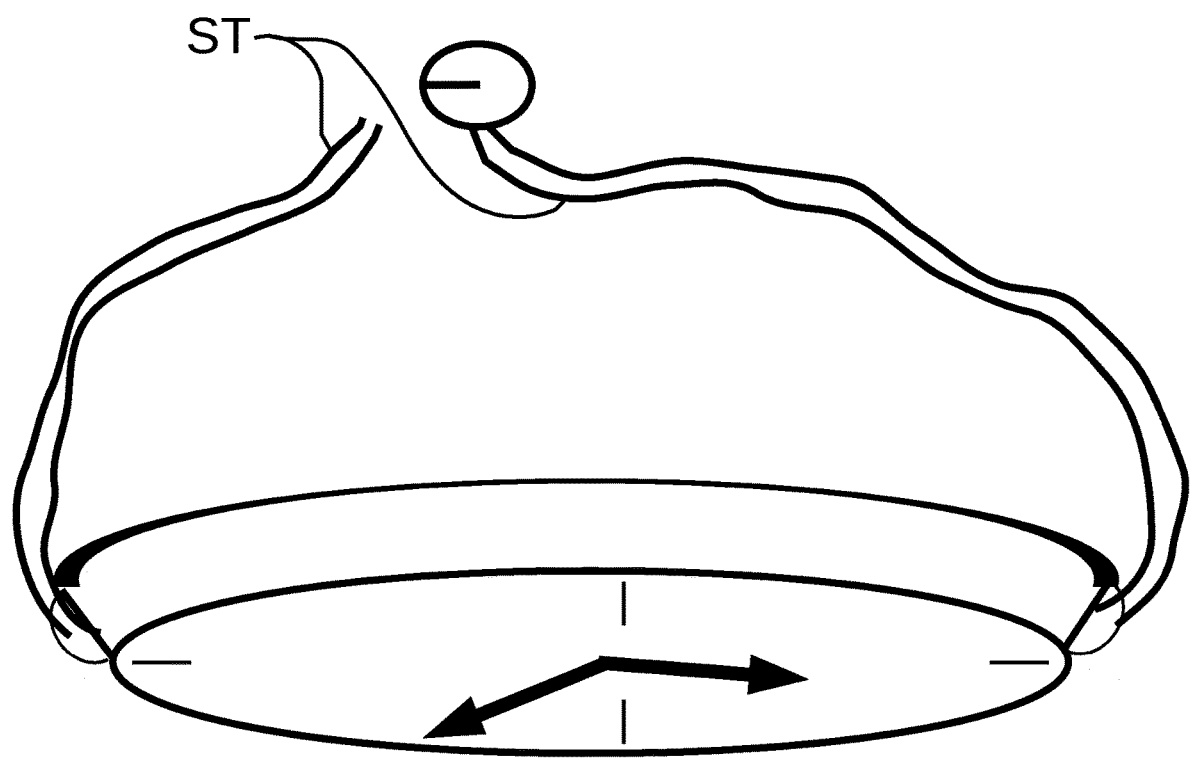
FIG. 7. Very, very old art, really old art! A wrist-watch type device adapted to show the time. Time keepers became important with the open ocean navigation and invasion of the Americas, because latitude, or north-south position, was always possible to determine easily by observing the height of certain stars above the horizon (say, the Northern Star), but the longitude could not be determined without the knowledge of the time at some reference place (say Greenwich or Paris), so a true clock or watch was crucial for navigating the open ocean, else the ship could run onto the shore at night and kill everybody on board.
Figure 8A:
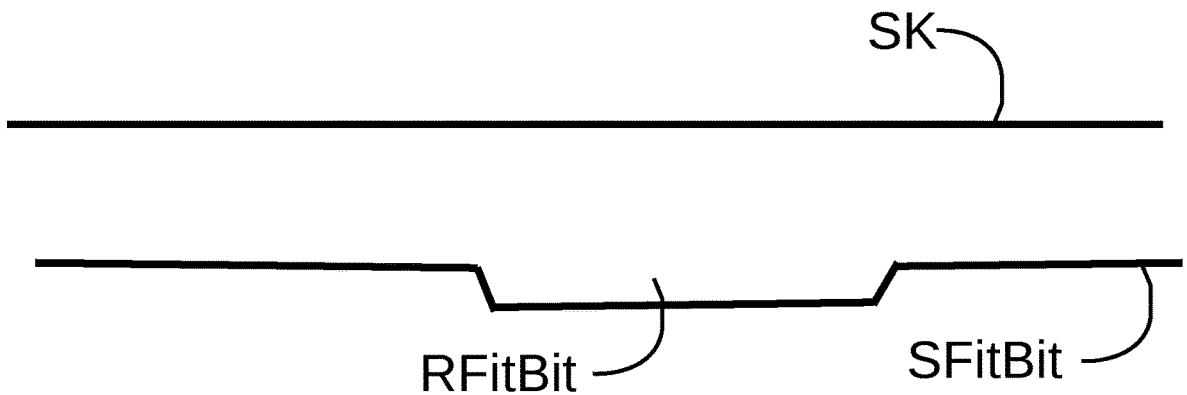
FIG. 8A. RFitBit=Re-entrance on FitBit, SFitBit=Surface of FitBit. View of the device of my invention away from skin surface.
Figure 8B:
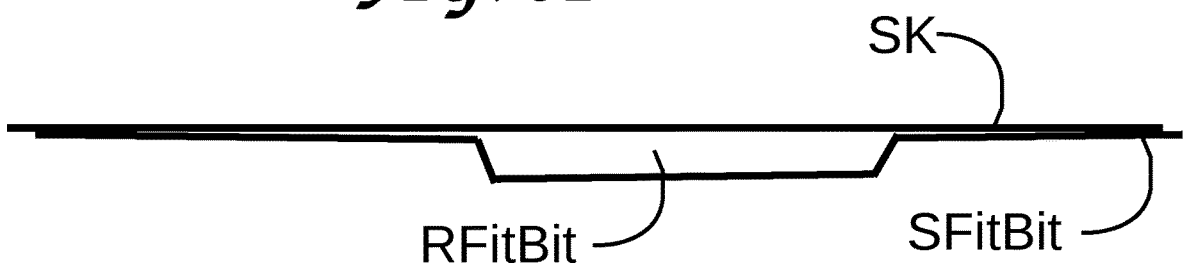
FIG. 8B. RFitBit=Re-entrance on FitBit, SFitBit=Surface of FitBit. View of the device of my invention touching skin surface FIG. 8C. RFitBit=Re-entrance on FitBit, SFitBit=Surface of FitBit. View of the device of my invention pressed against skin surface; skin adapts to contour of device of my invention, filling-in the re-entrant "hole" of the device of my invention.
Figure 8C:
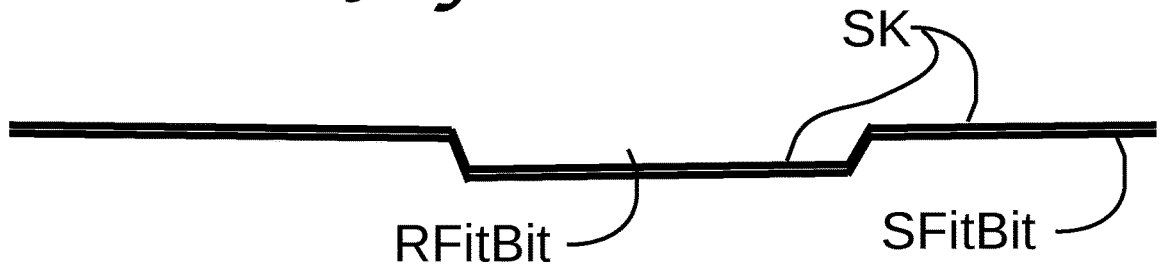

Referring to FIG. 1A and FIG. 1B, the main embodiment of our wonderful invention is a holding box or container (box), with strap holders (STH) capable of keeping attached in place straps (ST) adapted to keeping the container (box) in place and tight held against the wrist of the wearer, similar to the straps that keep wrist-watches in place. The main embodiment has two protruding blocks, or volumes or wedges, which are capable of holding in place a radiation emitter LE in a first protruding box, which emits a radiation beam LB, and a radiation detector LD1 in a second protruding box, capable of measuring the amount of energy, or the intensity, or the number of photons, of the radiation beam LB that reaches the radiation detector LD1. Some radiation that is emitted by the radiation emitter LE may be either (1) absorbed by or (2) scattered by the flesh or any cell, particularly the red blood cells circulating in the blood of the animal wearing the device. Radiation detector LD1 is capable of measuring the intensity of the radiation LB emitted by the radiation emitter LE that propagates through the flesh of the animal, including humans, that is pressed down into the space between the protruding blocks that hold the radiation emitter LE and the first radiation detector LD1. The main embodiment is also capable of holding in place an optional second radiation detector LD2, which is located at such a place that it is capable of detecting radiation scattered out of the main radiation beam LB by the scattering center SC1 towards the position of radiation detector LD2. Other detectors at different positions and angles are also possible to be included. Other shapes of the re-entrant cavity are equally possible, as with the smaller sides at some angle different than 90 degrees with the longer dimension, or with curved shape re-entrant cavity, there included spherical, ellipsoid, and no-named curve shapes. It is also possible to have the surface of the holding box (box) as a single flat surface (no re-entrant cavities, no protruding blocks), while positioning the radiation emitter LE at a shallow angle with the box's surface (that is, with the skin of the wearer) and the radiation detector LD at a shallow angle as well, as seen at FIG. 2, FIG. 3, FIG. 4, FIG. 5, FIG. 6, FIG. 1A, FIG. 1B show several views of the main embodiment of out wonderful invention. These figures are all assuming a particular possible embodiment of our invention, which is for use strapped on the wrist of a humans, similarly to a wrist watch, similarly to most fit-bits, as depicted at FIG. 7. It is worth to refer to FIG. 7, a wrist-watch, for the reader to keep in mind the structure and size and possible meaning of each element, yet the invention is not restricted to be worn on the wrist, it being possible to position the device of our invention in other parts of the body as well, as around the upper arm, around the elbow, around the upper or lower leg, etc. Referring to FIG. 1A, one can see a perspective view of the main embodiment of our invention NOT attached to any animal or humans. Looking at FIG. 1A one can see that our wonderful invention sports two protruding blocks, one which contains a light emitter LE, the other that contains a light detector LD1. The reason for the protruding feature can be understood looking at FIG. 4, which also depicts our amazing invention, this time strapped on the wrist of a human. In this FIG. 4, which depicts a cross-section of an arm of a human, at the distal end of the arm, which is the normal position for a wrist watch or a fit-bit, one can see the two bones, radius and ulna, and our amazing invention strapped on the wrist, pressed in place, which then causes that the flesh of the human penetrates the re-entrant cavity between the light emitter LE and the light detector LD1. The reader is invited to follow the line SK of the skin of the wearer, and the line SF of the surface of the device of our amazing invention; the skin line SK follows closely the surface line SF because the supporting device of our invention is pressed against the wrist of the wearer. An idealized situation of this is shown at FIG. 8A, FIG. 8B and FIG. 8C. In these FIG. 8A, FIG. 8B and FIG. 8C the reader can see the skin of the animal away from the surface of the device of our invention at FIG. 8A, then the device of our invention just touching the skin of the animal, but not being pressed against the skin, at FIG. 8B, then, finally, the device of our invention pressed against the skin of the animal at FIG. 8C, which causes that the flesh of the fitbit user penetrates the re-entrant cavity RfitBit. Naturally that for such a penetration to occur the depth of the reentrant cavity needs to be small or shallow, say, 1 mm, or 2 mm. This last case shows the flesh of the animal penetrating the cavity RfitBit. This penetration is necessary to cause that the radiation beam LB propagates through the flesh of the person who wants his heart beat measured.

Figure 4:
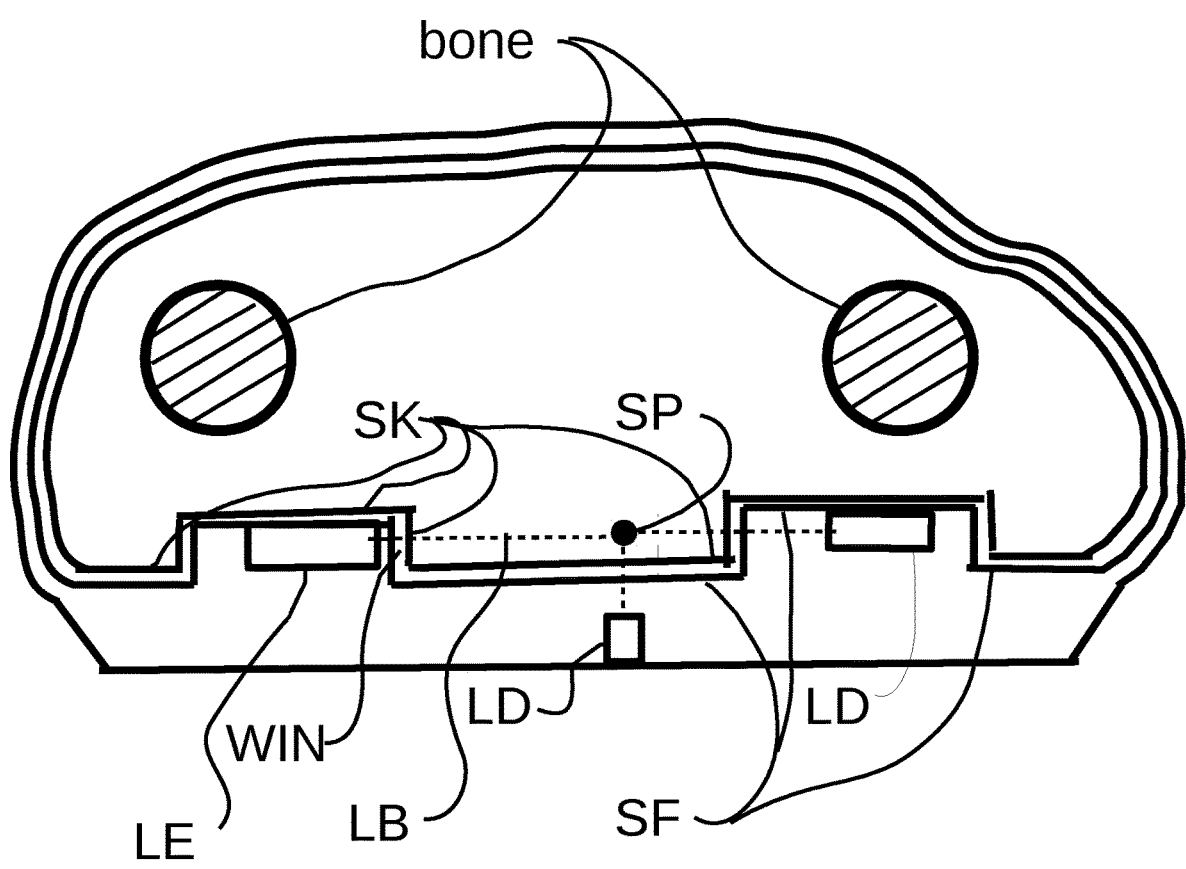
FIG. 4. Fitbit-type supporting structure shaped to encase itself around the wearer's wrist with the objective of emitting a light beam LB that crosses the window WIN then penetrates the body at normal (90 degrees) incidence. Beam LB may suffer scattering events at scattering center SC (SP), being partly scattered forward, partly scattered at almost 90 degrees, to be detected at light detectors LD.
Figure 5:
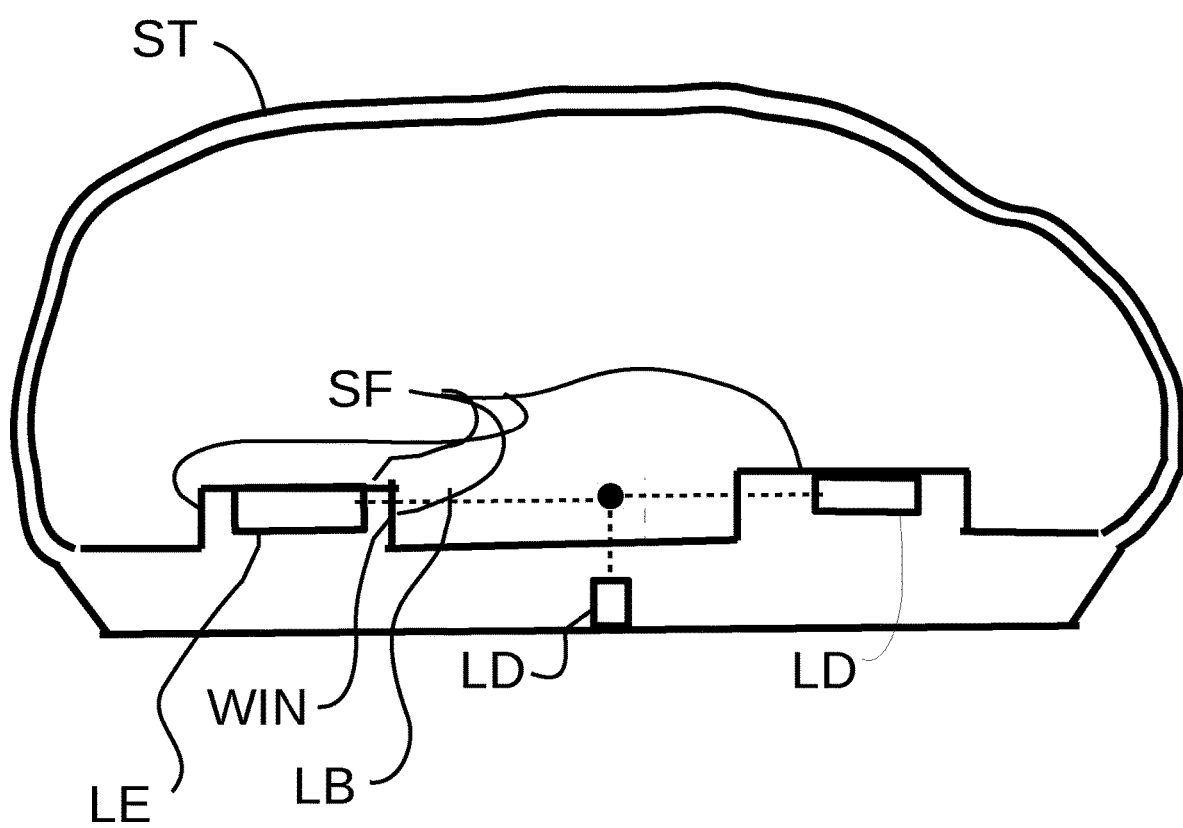
FIG. 5. Fitbit-type supporting structure shaped to encase itself around the wearer's wrist with the objective of emitting a light beam LB that crosses the window WIN then penetrates the body at normal (90 degrees) incidence. Beam LB may suffer scattering events at scattering center SC, being partly scattered forward, partly scattered at almost 90 degrees, to be detected at light detectors LD.
Figure 9A:
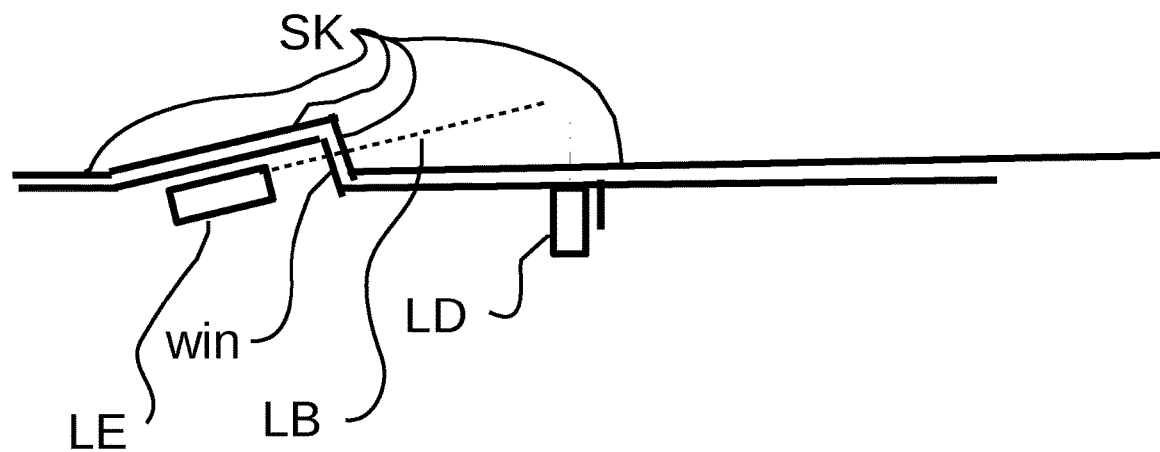
FIG. 9A Fitbittype supporting structure shaped to encase itself in the wearer's body with the objective of emitting a light beam LB that crosses the window WIN then penetrates the body at normal (90 degrees) incidence.
Figure 9B:
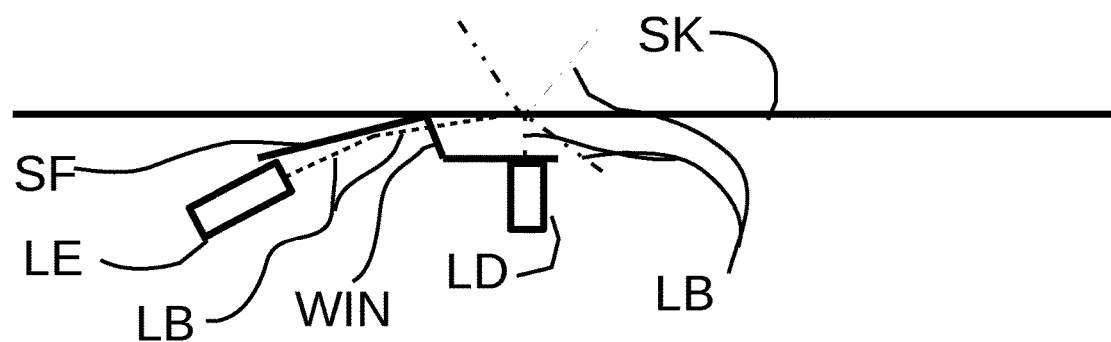
FIG. 9B. Laser emitting light beams redirected by total internal reflection at lower (inner) side of sf and normal (perpendicular) light detectors ahead of beam.

If it is desired to measure the decrease of radiation along the incident beam direction, then the exit window near the radiation emitter LE and the window near the radiation detector LD1 should be made perpendicular to the propagation of the radiation. This is not necessary, but it is one of the options protected in this patent. This is the preferred embodiment, as shown in FIG. 4, FIG. 1A and FIG. 1B, among others. But it is possible to have the window at such an angle that the radiation beam LB reaches the window at an angle other than 90 degrees, as shown at FIG. 9A and FIG. 9B, among others.

It is possible to make the measurement of blood volume using either the scattered radiation or using the radiation that suffered neither scattering not absorption events, which I call transmitted radiation—a non-standard use of the word, my personal use here, not used by anyone anywhere in the universe. Both of these are shown at FIG. 4, FIG. 6, FIG. 1A and FIG. 1B. Here it is a good time for a warning to the reader: you should keep in mind that typically both the scattering cross section and the absorption cross section go up-and-down together (remember that cross section is the physics speak for probability of). This means that where there is larger scattering (more radiation impinging on the off-incident direction radiation detector) there is also more absorption, which means that the transmitted radiation is smaller, since the initial radiation beam is decreased by both scattering and by absorption as well. This is most important, it meaning that the scattered radiation measurement is positively correlated with the "opacity" of the scattering centers, while the "transmitted" radiation measurement is NEGATIVELY correlated with the "opacity" of the scattering center!, and, saying it in different words: when the scattered measurement goes up in most cases the "transmitted" measurement goes down!, or, in still different words: the scattering measurement is a positive image of the points, while the "transmitted" measurement is a negative image of the points. The points together form the images, one which I call "scattered image" and other that I call "transmitted image", which are the negative of each other. They cannot be summed up to obtain a complete image! They can be joined into an image that uses all the information, but a mathematical manipulation needs to be performed on one or the other, before merging them!

Preferred Embodiment—FIG. 1A and FIG. 1B, and FIG. 3, FIG. 4 and FIG. 6 display some aspects of the preferred embodiment of our invention. These figures should be understood in view of FIG. 7, which is a watch, a normal, ordinary wrist watch, which is similar in shape to the fitbit of our invention. Then FIG. 10A, FIG. 10B, FIG. 11A, FIG. 11B, FIG. 9A, FIG. 9B, FIG. 12A, FIG. 12B, FIG. 23, FIG. 13A, FIG. 13B, FIG. 14, FIG. 15 depicts several variations of the main embodiment and some details of the main embodiment.

FIG. 7 shows a wrist watch, which is old art, as the lawyers say, or old stuff in common parlance—let us be real, it is not art at all! It is shown here only for the reader to identify the equivalent parts on the fitbit of our invention: a box, with either a clock-work mechanical system, or a battery and an electronics circuit, perhaps with added light sources and light detectors and other electrical transducers as well, the box being firmly kept at the wrist by either a long strap ST, with some mechanism to adjust its grip on the wrist, as a multiplicity of holes at one of the extremities of it, and a closed loop with a small sticking finger at the other extremity of strap ST. Alternatively, traditional watches and/or some fitbits sports two separate straps ST, each starting at one of the sides of the watch/fitbit at the holding part STH (see FIG. 7), in which case one of the straps ST is fitted with the holes at its distal extremity, and the other strap ST is fitted with the closed loop with a small sticking finger at its distal extremity. Our figures are drawn for this latter case of two straps ST, each starting at a holding piece STH on opposing sides of the FitBit, as it is the case of at least most, and I think all traditional wrist watches. It is understood that changing stripe ST to a single longer stripe does not change the nature of the invention.

Figure 6:
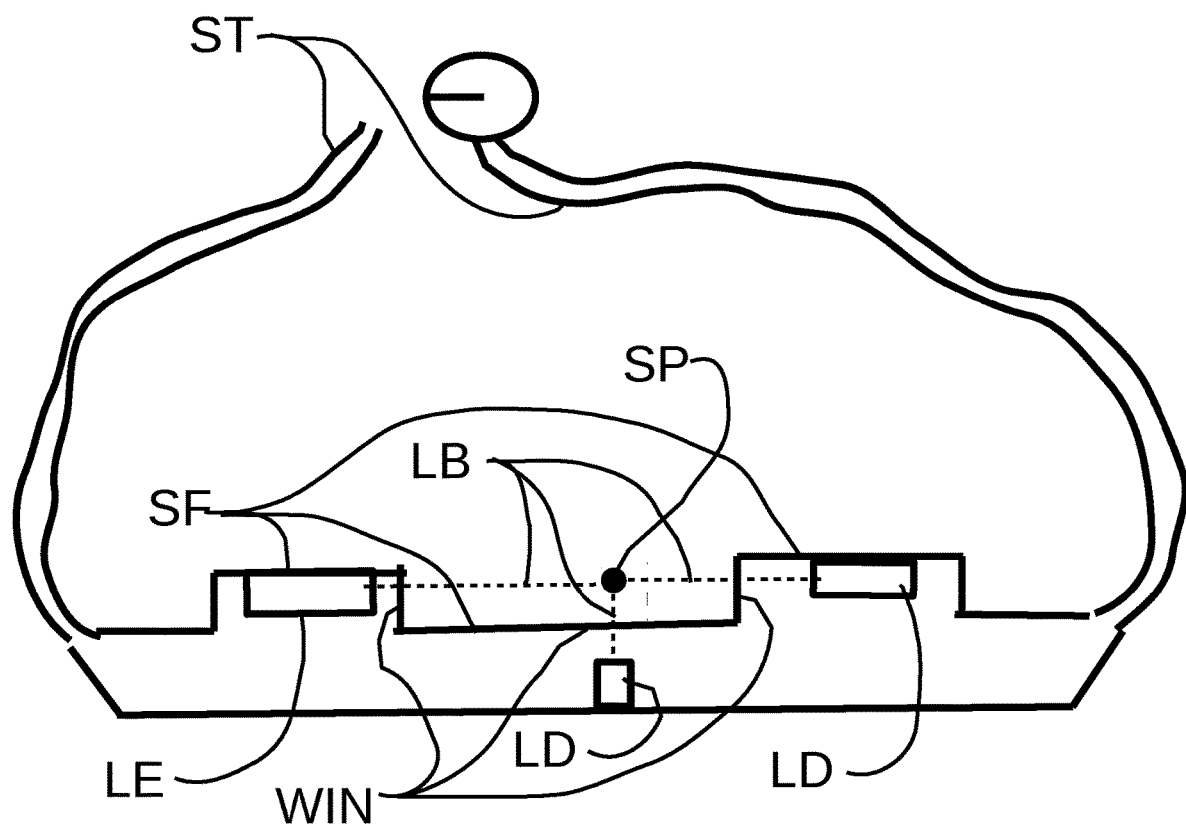
FIG. 6. Several elements of our fitbit-type device of our invention.

Referring now to FIG. 6, FIG. 1A and FIG. 1B the reader can see the fitbit of our invention. FIG. 1A and FIG. 1B shown our amazing improved fitbit, firstly in perspective (FIG. 1A) then, at FIG. 1B, a cross section of the fitbit of our invention at the plane A-A', which is shown in the FIG. 1A.

Such a design for the amazing FitBit of our invention causes that when the device is firmly attached on the wrist of the wearer, so as to be pressed against the meat, some of the wearer's meat penetrates the volume between the radiation emitter LE and the radiation detector LD1.

FIG. 10A, FIG. 10B, FIG. 9A, FIG. 11A and FIG. 11B depict variations of the same hardware. The reader is warned that in many of these figures, e.g., FIG. 10A, FIG. 10B and FIG. 11A the device surface SF is drawn away from skin SK, which is an exploded view, this having been done only to clearly show the different parts: the mechanical support of the main embodiment and the skin near which the mechanical support is attached. For the main embodiment the device is either a fitbit firmly fixed on the wrist of a person in such a way that the extruding protuberance with the window WIN is pressed against the flesh forcing itself into the flesh, or else there is a re-entrant surface on the external surface of the supporting structure, which is such that, when the fitbit is firmly attached to the wrist the flesh of the wearer penetrates the re-entrant cavity. Either way, the radiation emanating from the fitbit propagates from a transparent window WIN into the skin SK and flesh of the human wearer at an incidence angle of 0 (zero) degrees. The reader is here again reminded that the radiation in the main embodiment is "light", as red light, infrared light, etc. The width of window WIN is, for the main embodiment, of the order of 400 micrometers, but variations for more and less are possible without changing the invention. This value of 400 micrometers is chosen as a best value because it is enough to allow the light beam LB to exit the fitbit device, and also small enough that the protuberance at WIN is small enough to indent itself in the flesh of the wearer while not to cause discomfort on the wearer. This detail of keeping the window WIN pressed against the flesh of the wrist of the wearer is important for the invention to work, because of the inevitable light beam LB propagation direction change if LB meets the skin of the wearer at any angle other than 0 degrees (perpendicular incidence). This no-deflection characteristic guarantees a known light beam propagation at a desired and known propagation path, almost parallel to the skin and just under the skin, propagating forward at depths ranging from 0.5 mm to 3 mm. This main embodiment is shown at FIG. 9A, but FIG. 9A is a blow-out rendering of the situation, with the fitbit device separated from the skin (as opposed to be pressed against the skin), which is done only to clearly show the parts and how they interlock. The reader will notice that the shape of the skin in FIG. 9A follows the shape of the fitbit, exactly because FIG. 9A is a blow-out rendering, in which the skin at the wrist of the wearer assumes the shown shape only because the flesh, being soft as it is, adapts to the shape of the harder surface of the fitbit that is pressed against it—and the reader should keep in mind that the protuberance at window WIN is of the order of 400 micrometers (less than ½ mm), easy to insert itself into the flesh.

Figure 10A:
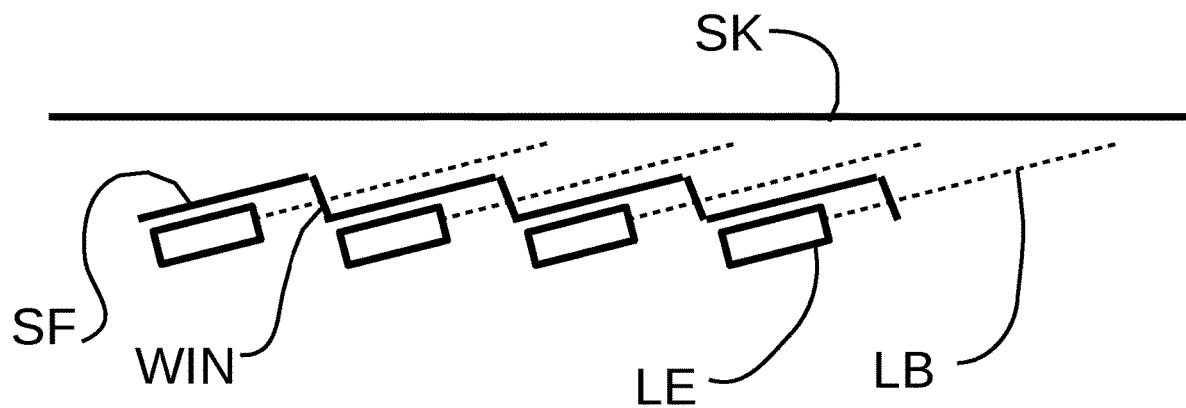
FIG. 10A. Laser emitting light beams at grazing angles with skin.
Figure 10B:
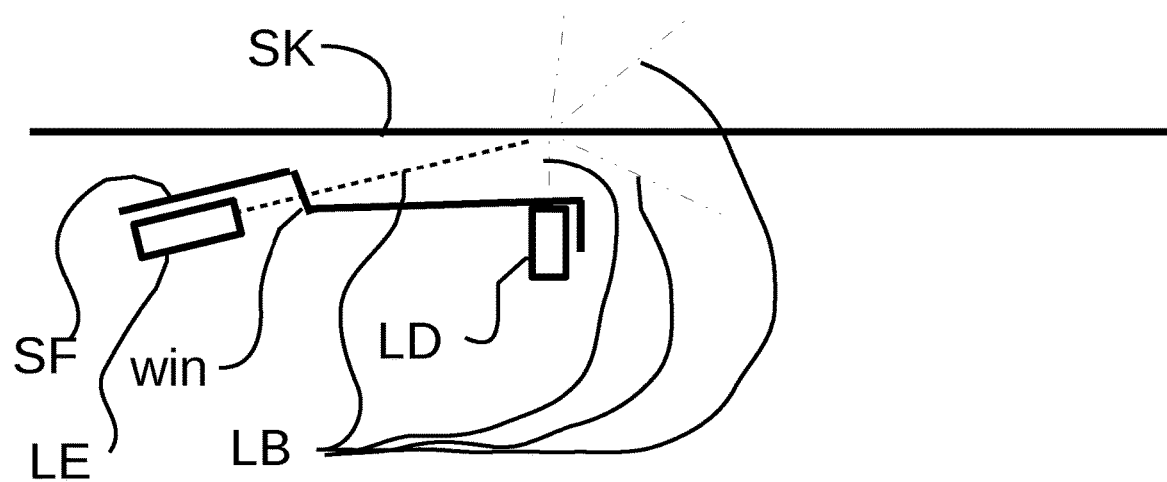
FIG. 10B. Laser emitting light beams at grazing angles with skin with normal (perpendicular) light detectors ahead of beam.
Figure 11A:
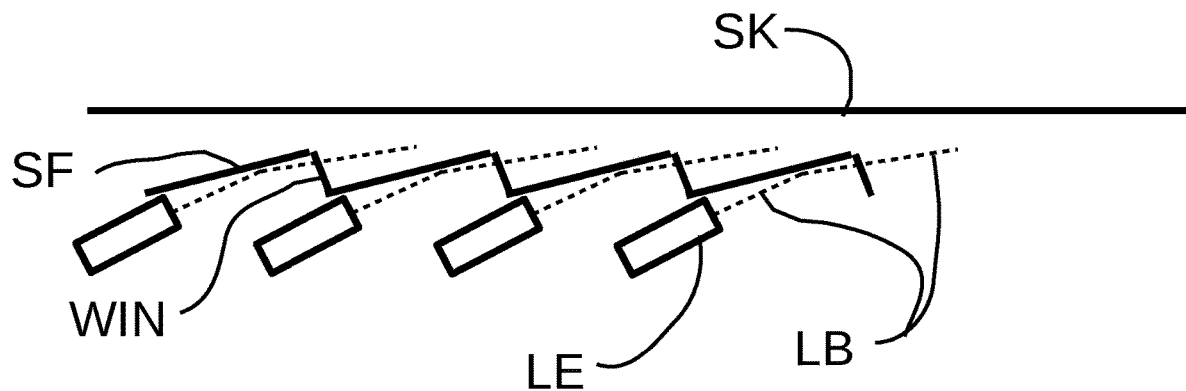
FIG. 11A. Laser emitting light beams redirected by total internal reflection at lower (inner) side of SF.
Figure 11B:
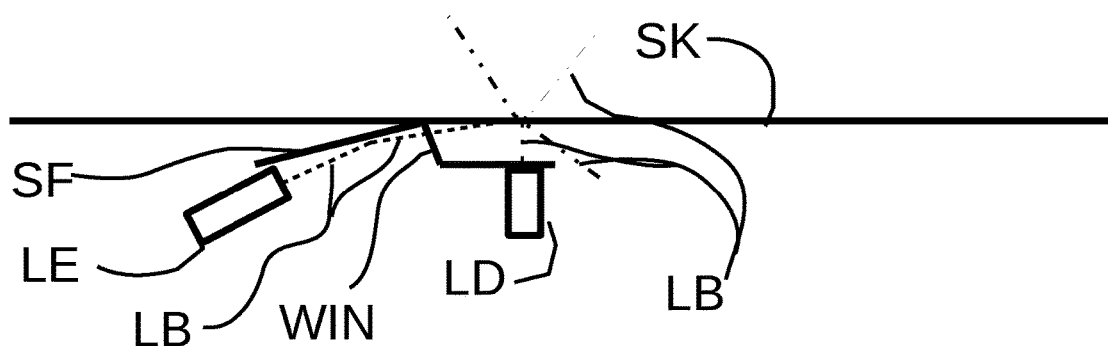
FIG. 11B. Laser emitting light beams redirected by total internal reflection at lower (inner) side of SF and normal (perpendicular) light detectors ahead of beam.
Figure 12A:
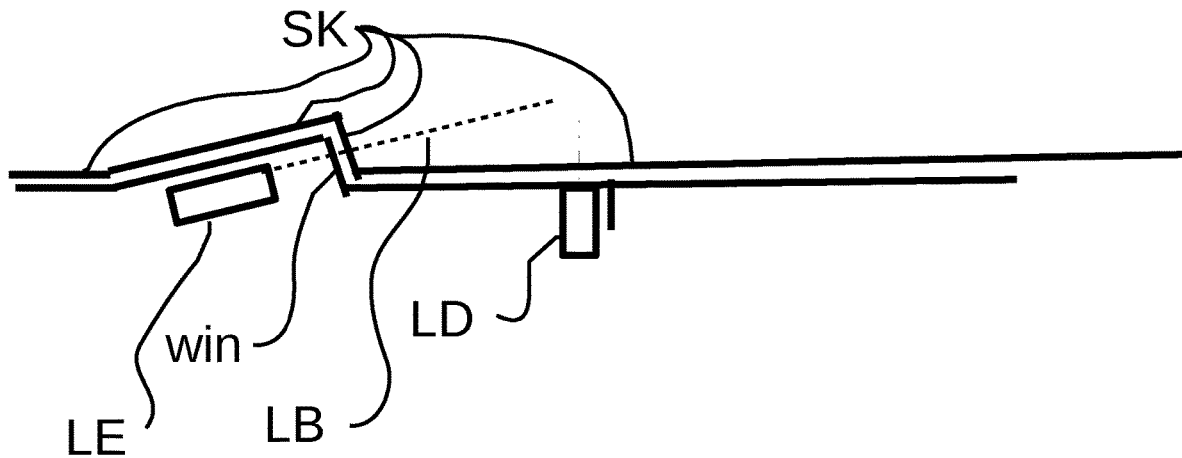
FIG. 12A. Fitbit-type supporting structure shaped to encase itself in the wearer's body with the objective of emitting a light beam LB that crosses the window WIN then penetrates the body at normal (90 degrees) incidence.
Figure 12B:
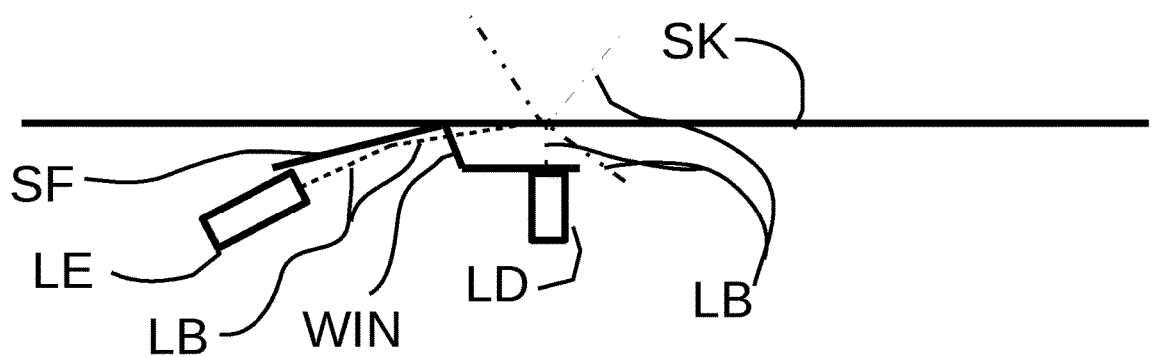
FIG. 12B. Laser emitting light beams redirected by total internal reflection at lower (inner) side of SF and normal (perpendicular) light detectors ahead of beam.

FIG. 11B shows the device touching the skin, as it does during normal use. So, repeating with other words as a rampart against lawyers, attorneys, slimes and their likes, FIG. 10A, FIG. 10B and FIG. 11A show the device of our invention separated from the skin, this being done only for the purpose of clearly show what is our invention (we did not invent the skin sk). Only FIG. 11B shows our invention correctly positioned against the skin SK, as it has to be during use, similarly to all fitbit devices.

We want to warn here the reader that in all these figures the penetration of the probing "light" is small if compared with the other dimensions of interest in the drawings. To respect this, and also to simplify the drawings, the dashed lines that indicate the propagation of the "light" beams show a light bean propagating back into the light detector LD as being scattered at the outer surface of the skin, when in reality though some scattering occurs at the surface of the skin, what matters for the invention is scattering that occurred inside the body, as shown in FIG. 9B. So the reader is now aware that most figures will indicate a scattering at the very (outer) surface of the skin, when in fact what we mean is scattering that occurred just a little inside, or under the skin as depicted at FIG. 9B. Lawyers and other vermins, please do not come to annoy me latter on this, please, please.

Figure 15:
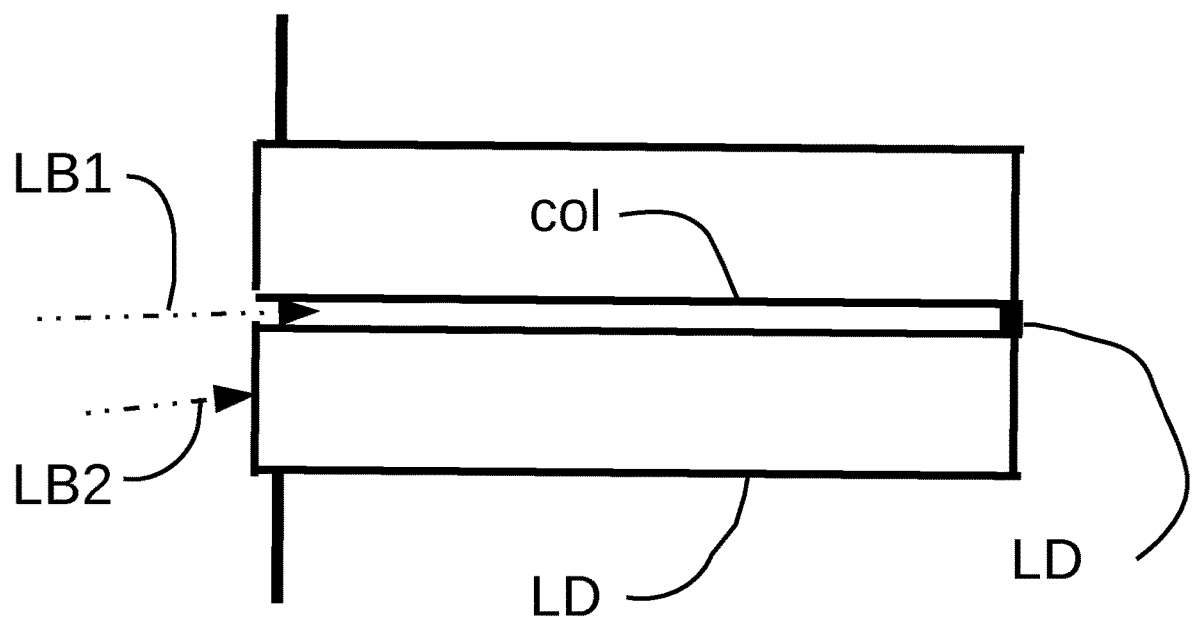
FIG. 15. Light detector of our invention with the detecting element at the end of a cylinder that acts as a collimator COL, preventing "light" from reaching the light detecting element LD unless it is propagating along a certain preferred direction (within a defined angular aperture).

Referring now to FIG. 15, light detector LD may include a collimator (col) to block "light" propagating from unwanted directions, to enter and being measured by LD. The reason for this is that the image is supposed to be of objects and features at a certain direction with respect to the light detector LD, usually directly in front of LD. FIG. 15 show one example of such a feature, with the light detecting element (LDE) at the end of a collimator (col), which collimator substantially blocks "light" propagating from unwanted directions from reaching the light detecting element (LDE) and being measured as a desired "light". As shown in FIG. 15, a "light" beam LB1, which is propagating along a desirable direction (from directly in front of LD) is capable of reaching the light detecting element (LDE) and be measured, while another "light" beam LB2, which is in such a direction that it would have reached the light detecting element LDE and be measured, is NOT capable of reaching the light detecting element (LDE) at the end of the collimator (col) and is therefore not counted. Throughout this patent application it is understood that a light detector LD may be of this more complex design as shown in this FIG. 15, including a collimator, or instead of a simple light detector. Also, such a collimator may be an integral part of the light detector LD, as in FIG. 15, or it may be a separate part kept in front of a single detector or an array detector, as a CCD, both possibilities being able to accomplish the same objective of keeping out unwanted "light".

We will use FIG. 10B to describe the preferred embodiment of our invention, but it is understood that many variations are possible, some of these variations shown in the figures that are part of this patent application, and others variations, as per lawyers' approaches, tricks and deceits, are not shown, but intended to be covered by this patent application. The preferred embodiment is a mechanical support box that is held against the skin SK of an animal (usually a human), with a light emitter Light Emitter (LE) that emits a radiation at a direction close to, but not completely, parallel to the skin SK of the animal, and with a light detector (LD) a short distance in front of the light beam LB from the point of contact between the light beam LB and the skin sk. In the preferred embodiment the mechanical support that is held against the skin SK is a fitbit device, and the skin SK is at the wrist of the animal. The radiation emitter is preferentially a light emitter LE, which is preferentially a laser, but many other source are possible and compatible with our invention, and the light emitter LE is preferentially along a direction that is almost parallel to the skin sk, say at an angle of 10 degrees with the direction of the skin sk, though this particular value is not the only one that is possible for our invention to work. Of course that it is also possible that the direction of the light emitter LE is any direction, the device including mirrors so positioned that the light beam LB is redirected to a direction substantially parallel to the skin SK of the animal. In general light beam LB should be almost parallel to the skin SK for the main embodiment, but variations, as described later, are possible, in which the light beam LB is not almost parallel to the skin SK, including the variation of the light beam being normal (perpendicular) to the skin SK. The light detector is preferentially positioned normal to the skin SK, as shown, but normal orientation towards the skin SK of the animal is not the only possibility, other orientations being possible and compatible with our invention. Normal here is used in the mathematical sense, which means perpendicular, as is well known to the readers versed in mathematics, and as defined in the definition section of this patent application.

The preferred embodiment uses a light emitter LE that emits infrared radiation of wavelengths in the preferred range of 850 nm+−50 nm, that is wavelenghts from 800 nm to 900 nm. Any chosen wavelength in this his range of 800 to 900 nm is best because of its higher penetration in animal cells, particularly its lower absorption and scattering cross-sections by the pigment melanin, which is more abundant in humans of darker skin, to the point that existing fitbits fail to work for darker skinned persons.

The direction of propagation of the light beam LB is important for this invention to work because if the light beam LB is sent normally (perpendicularly into the skin) then the infrared photons penetrate too deep, into depths where there is less variation in blood irrigation that changes with each heart beat, resulting in that there is only a small variation in the intensity of the infrared back-scattered and the device does not work either, even if the light beam LB penetrate beyond the melanin layer. Note that my invention does not depend on this theory of the depth of penetration to be correct, but only in the experimental results from the inventors' experimentations. Moreover, though the invention itself came from pure cerebration, the actual confirmation by experiment is all that matters for the patent application, not the theory of why it works, not the process of cerebration that brought the solution of the problem to the attention of the inventor.

When the light beam LB is propagating parallel and just below the skin, then the infra-red photons are mostly in a path where the change in blood irrigation suffers maximum variation with each heart beat. This is so even if some photons happen to penetrate deeper below the skin, due to both the initial beam angular divergence and also due to forward scattering. It then follows, from this geometrical configuration and maximum interaction that matters for the working of this invention, that the variation of scattered infra-red photons is larger than other paths of photon propagation, particularly larger than photons propagating perpendicularly into the and below the skin sk. Another advantage for using this path of propagation which is almost parallel and just below the skin SK is that photons propagating along such path needs to be scattered by 90 degrees to be measured by the light detector LD, as opposed to be scattered by 180 degrees (completely backward), as is the case with most existing fitbits. It happens that the scattering cross section as a function of the angle of scattering is generally a monotonically decreasing function of the scattering angle, which then implies as per FIG. 13A and FIG. 13B, that there is less photons to measure when the illumination is perpendicular to the skin SK (180 degrees scattering, FIG. 13B) than when the illumination is just below the skin SK, almost parallel and just under the skin SK (90 degrees scattering FIG. 13A), as is the configuration of our invention. According to the measurements taken by the inventor, such a parallel propagating light beam LB produces maximum variation in the total energy of back-scattered photons. We warn the reader that we are here using the technical language used in physics, because in common language this would be said " . . . produces maximum variation in the total energy of the sideways (90 degrees) scattered photons.". In physics, all photons scattered at an angle larger than 90 degrees with the directions of propagations are called back-scattered— though this statement is misleading when taken literally in common English. This physics wording happens because we physicists call anything that is scattered into the forward hemisphere (less than 90 degrees deviation with the initial beam) forward scattering, and accordingly, anything that is scattered into the back hemisphere (more than 90 degrees deviation with the initial beam) back-scattering.

Figure 2:
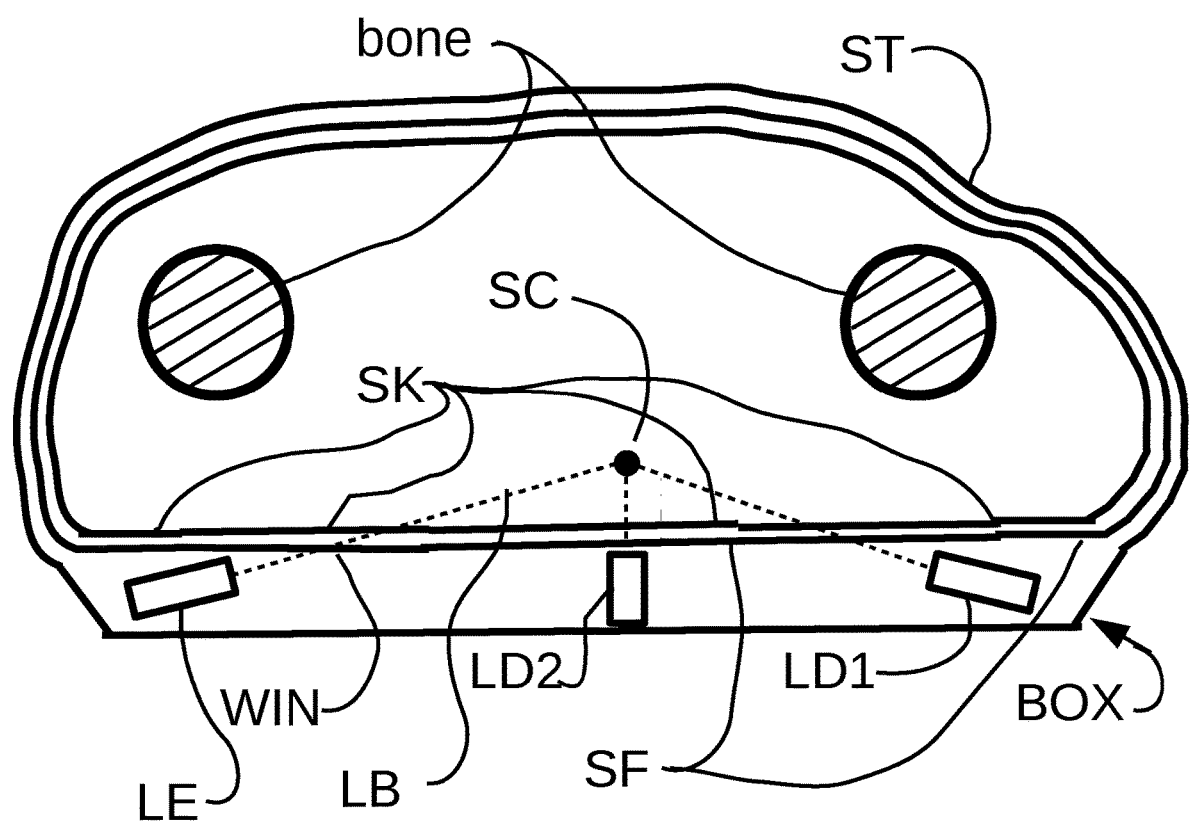
FIG. 2. Fitbit-type supporting structure shaped to encase itself around the wearer's wrist with the objective of emitting a radiation beam LB that crosses the window WIN then penetrates the body just under the skin SK. Beam LB may suffer scattering events at scattering center SC (SP), being partly scattered forward, partly scattered at almost 90 degrees, to be detected at radiation detectors LD1 and LD2.
Figure 3:
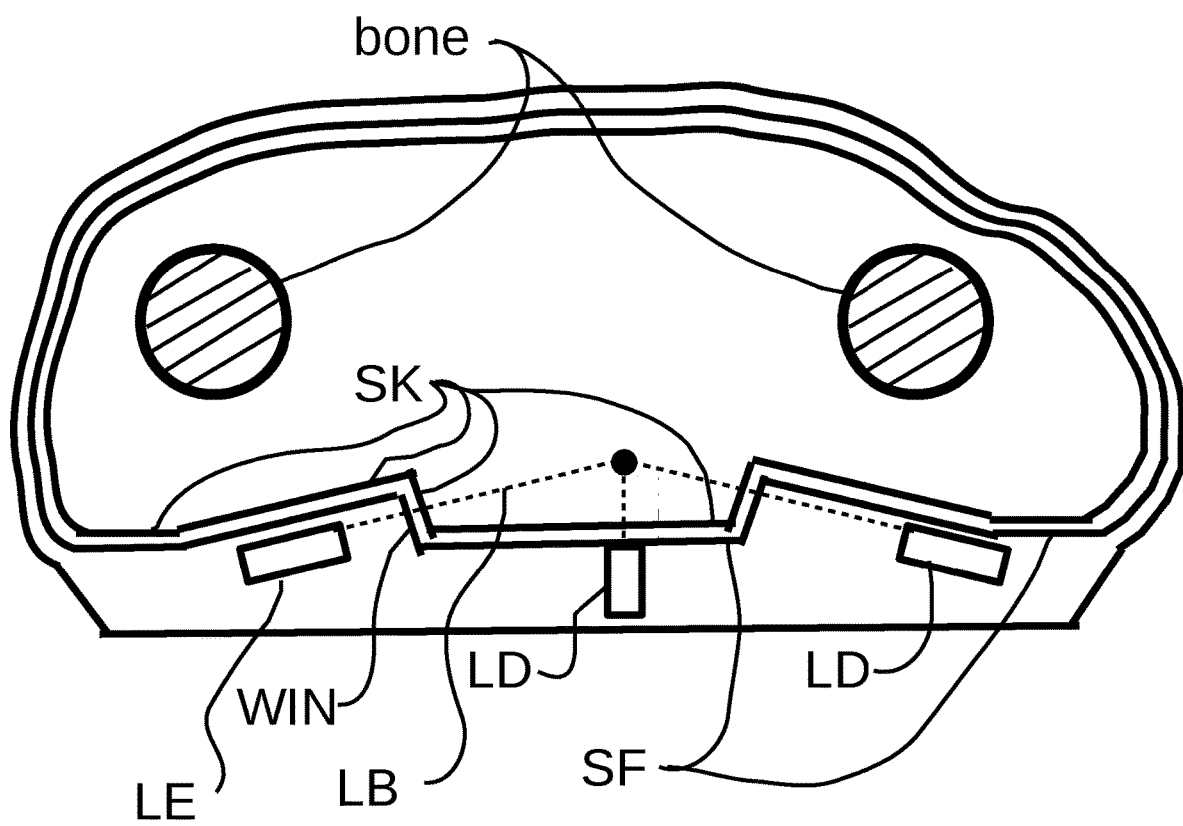
FIG. 3. Fitbit-type supporting structure shaped to encase itself around the wearer's wrist with the objective of emitting a light beam LB that crosses the window WIN then penetrates the body at normal (90 degrees) incidence. Beam LB may suffer scattering events at scattering center SC (SP), being partly scattered forward, partly scattered at almost 90 degrees, to be detected at light detectors LD.

The position of the light emitter LE is fixed with respect to the skin SK of the user by the surface of the mechanical support, which, in the preferred embodiment is a fitbit-type device, as shown at FIG. 3, FIG. 4 and many others.

The depth of the indentation on the fitbit surface, which is the width of the window WIN, is typically of the order of a fraction of a millimeter to a millimeter or two, and the corners of the indentation or almost-perpendicular surface are rounded to prevent scratching the skin of the fitbit user. Window WIN is, on the preferred embodiment of our invention, perpendicular to the direction of the light beam LB. This is another important feature to prevent causing discomfort on the fitbit wearer.

Light detector LD receives light scattered from the region under the skin of the wearer. The intensity of this light scattered into the light detector LD varies with the amount of blood in the region from where the light beam LB is scattered, causing a periodic variation of the light intensity detected (measured) by light detector LD. This periodic variation of the light intensity follows the heart beatings. This periodic variation can be measured, converted by an ordinary ADC (analog-to-digital converter), then the digital result can be transferred to a microcontroller and counted over any convenient time period, say, 15 seconds, or 30 seconds or any other time. After normalizing the number of variations to 60 seconds, this normalized counting is the number of heart beatings per minute (one minute is 60 seconds). Any ordinary microprocessor, which is already part of the existing fitbits, can do this process of "watching" the periodic variation of the light intensity at the light detector LD.

Examples of Intended Uses

One example of intended use is to monitor the heart beating rate of humans wearing fitbit-type devices intended to acquire data about their physical activity, either for heath reasons or for the purpose of improving their physical performance or even just to show-off.

Another intended use of the device of our invention is to buy a home for the inventor.

DETAILED DESCRIPTION—Operation of Invention

I am adding a theoretical analysis of the invention because it helps the reader to better understand the invention and also to reproduce it. It is my view that a clear understanding of the structure that will be described in the sequel is only complete with an understanding of the reasoning underlying it, as opposed of a simple and magic physical description of the device—amazing as it is! The method of our amazing invention is to direct the energy probing beam to a propagating path just under the skin of the fitbit wearer, that is, propagating generally parallel to the skin and just under the skin, say, from 500 micrometers (0.5 mm) to 5 millimeters under the skin, preferably 500+−200 micrometers under the skin. The probing beam is preferably either visible light, or even better, what is known as deep red (red near the end of the visible red, around 700 nm), or even better, near infrared radiation, preferably near 850 nm. The reasoning for this is discussed and explained in the theoretical analysis below, it has to do with the smaller absorption by flesh of photons of these wavelengths.

Our invention operates on the differential cross section between blood and other animal cells, particularly between blood and flesh. This statement, which is written in physics language can be re-stated in normal English as "Our invention operates on differences of scattering properties, or probabilities, between blood and other cells of animals".

We note here that this is no difference between all our vision system that we use all the time for all things, and image detection hardware used by the hardware and the computer of our invention. It is what we do all the time from observing a painting on a museum or to read the letters in this funny written patent application. We decide that something is a leaf and not a flower both using the form of them and also using their color, i.e., using the differences in scattering of each for different colors. For example, most leaves scatters green light, some of which enters our eyes, absorbing the rest (red, yellow, etc.), while most flowers scatters a particular color, say red (as a red rose does), some of which red eventually enters our eyes, absorbing the other colors (yellow, green, etc.). In the case of our invention, as long as blood has a different scattering cross section (this is technical language, meaning probability of scattering, or power to scatter, or capacity of scattering), then the scattered "light", which is preferentially infrared "light" for the main embodiment of our invention, will show the difference, as detected by a camera, and later measured by a computer. It is this simple, no big deal! . . . .

The preferred embodiment of our invention uses near infrared radiation, with wavelengths in the window from 800 nm to 900 nm, because this range of wavelengths penetrates more in flesh, being, therefore able to probe deeper than other "colors". For example, many fitbits use green light, which is so much absorbed by melanin that it cannot penetrate (and come back out after scattering!) enough to show any change in absorption and scattering cause by any change in blood irrigation due to heart beatings. It is a known fact that these fitbits that use green light works from poorly to not at all for darker skinned people.

Figure 13A:
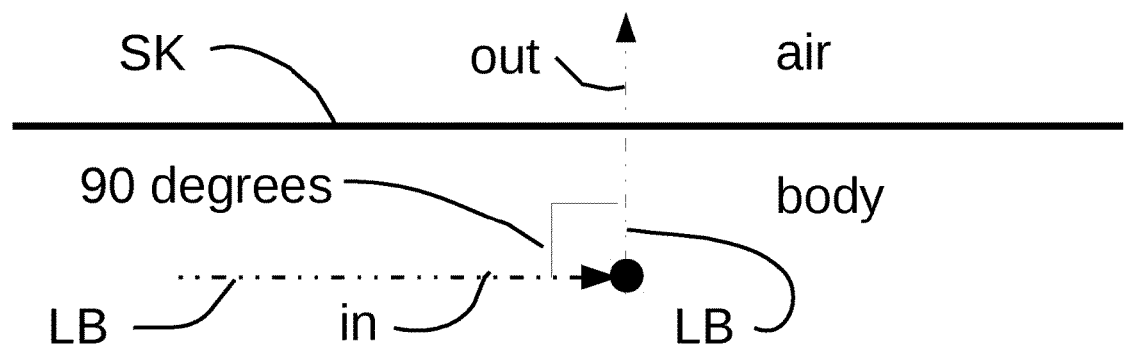
FIG. 13A. 90 degrees scattering from a light beam LB propagating just below the skin SK.
Figure 13B:
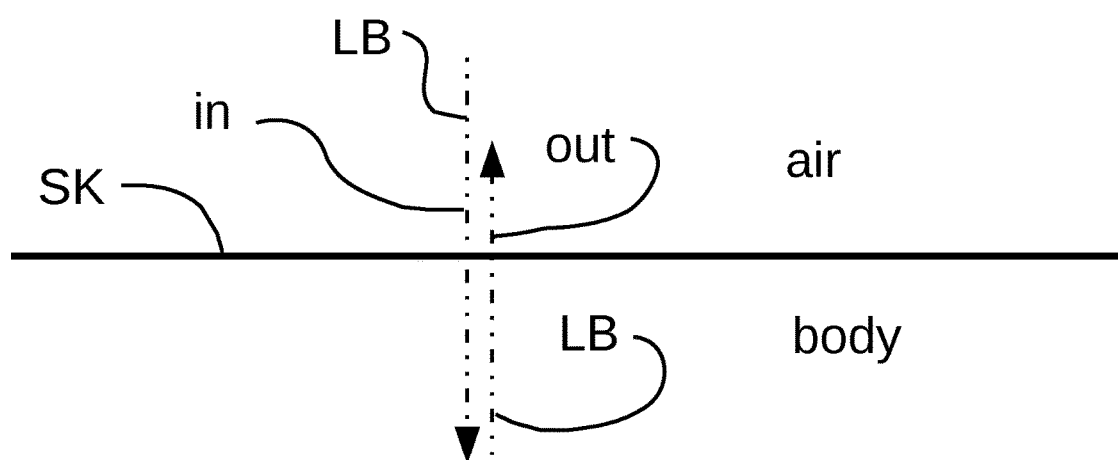
FIG. 13B. 180 degrees scattering.

Besides using infrared "light", our invention uses a "light" beam that propagates parallel to and just below the skin, as opposed to propagate into the body, or, in other words, that propagates parallel to and just under the skin, as opposed to propagate perpendicularly to the skin. The reason for this is different than the depth of penetration. Our invention uses a beam propagating parallel and just under the skin SK, because of two independent reasons. Firstly because it is just under the skin that occurs the largest change in blood irrigation with each heart beat, or with each increase in blood pressure at each systole (systole means the higher blood pressure, or the heart contraction). To say it in a different way, our invention uses a "light" beam parallel and under the skin because it is there, just under the skin, that occurs the largest change in blood irrigation with each heart pumping, and consequently there is the largest change of the measured quantity: the amount or intensity of scattered "light". Secondly, our invention uses a "light" beam propagating parallel to and just below the skin because with this path of propagation the scattered "light" has to suffer a scattering event of between 0 (zero) to 90 degrees to be measured by a light detector LD out of the body, instead of a 180 degrees scattering event, as it is the case for a light beam propagating perpendicular into the body, as used by most existing poorly designed fitbits. This makes a sizable difference for the measurement because in just about all cases, and it is so in this case, the scattering cross section (meaning, the scattering probability) is much larger for a 0-to-90 degrees scattering than for a 180 degrees scattering, so the geometric arrangement of our invention causes that more "light" reaches the light detector LD than the existing fitbits that illuminate the body of interest with perpendicular light then receives 180 degrees scattered light! It is this simple . . . . This is illustrated in FIG. 13A for a 90 degrees scattering and FIG. 13B for a 180 degrees scattering. This latter, FIG. 13B, 180 degrees scattering is what many would call back scattering in normal, ordinary, common English.

DETAILED DESCRIPTION—Description and Operation of Alternative Embodiments

Figure 14:
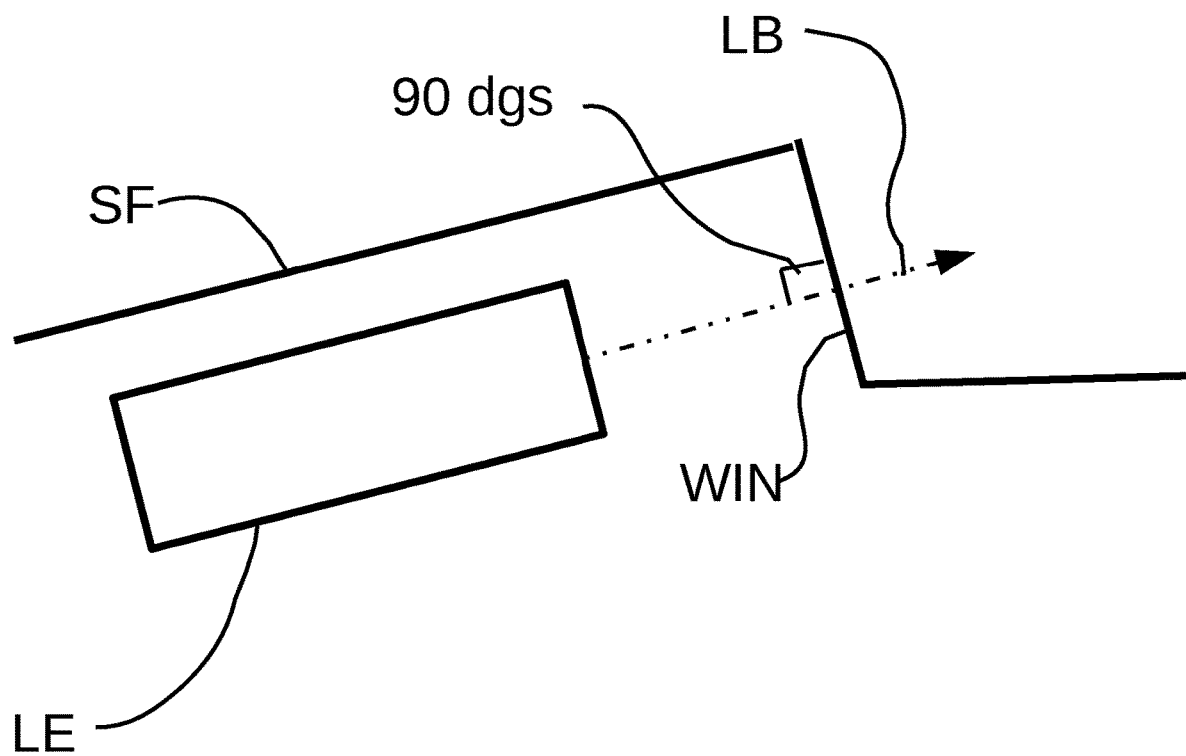
FIG. 14. Detail showing light emitter LE, light beam LB, surface SF and window WIN. Window WIN is preferably perpendicular to the light beam LB, as shown here.

FIG. 14 shows a detail of the mutual positioning of the light emitter LE, the light beam LB and the window WIN, and the preferred angle between the light beam LB and the window WIN, which is, for the main embodiment of this invention, preferably 90 degrees, as shown. The reason for this is to prevent multiple reflections at the entrance and exit surfaces of the window WIN.

Definitions

We start the detailed description with a definition of the most important terms used in this document. We do so to follow the spirit of the USPTO requirement of making a complete description of the device, so as not to leave doubt of the meaning of the terms we use.

CONCLUSION, RAMIFICATIONS, AND SCOPE OF INVENTION

It is worth to mention that another class of devices, to form images using infrared (mostly) in transmission and forward scattering is besieged by the same problem as the propagation of the infrared from the fitbit into the wrist, and both require solutions that are different in design but require the same principle of solution.

"Thus the reader will see that the illuminator of our amazing invention that so much improves the data collection for fitbit-type devices provides a highly reliable, lightweight, yet economical device that can be used by persons of almost any age and skill. In particular the illuminator of our invention contributes for the device, fitbit or any of its variations, to be usable for individuals of darker skin complexion.

While my above description contains many specificities, these should not be construed as limitations on the scope of the invention, but rather as an exemplification of one preferred embodiment of the invention. Many other variations are possible. For example, the light source may be of other colors, as visible red, which, though being more absorbed by the skin, including melanin, is still less absorbed than other colors of shorter wavelengths, as green, etc. The shape of the light emitted by the light source may also be altered in many ways. For example, the light beam may be spread along one direction only by a cylindrical lens (also known as astigmatic lens and non-spherical lens), capable of illuminating the body with a light "sheet" so to say, or a light distributed spread along a sheet parallel to, and slightly under the skin of the individual. Such a light distribution has the advantage of producing scattering from a wider area, therefore reaching more capillaries that are capable of producing the required optical signal when compared with a beam that is narrow, or laser-like, which by necessity probes a smaller number of capillaries than the sheet-like light beam.

Accordingly, the scope of the invention should be determined by the embodiment(s) illustrated, by the appended claims and the figures, and any lawyer's future confusing talk and their legal and illegal equivalents.

SEQUENCE LISTING

Not applicable.

The invention claimed is:

1. An apparatus for measuring a heart beating rate in animals, including humans, comprising:
   a) a holding and containing device adapted to hold, contain and maintain in fixed position against a skin of said animal a plurality of elements, where said elements are at least one from a set of said elements composed of:
      a1) at least one radiation emitting device, each said radiation emitting device emitting a radiation along a propagation path characteristic of each of said at least one said radiation emitting devices,
      a2) at least one radiation detecting device, each said radiation detecting device receiving said radiation from one or more said radiation emitting devices, along said propagation path characteristic of each of said at least one said radiation emitting device,
   b) a wrapping device adapted to keep said holding and containing device in fixed position against said skin of said animal, at some part of a surface of said animal, including said human,
   c) where said propagation path of said radiation emitted by said at least one said radiation emitting device defines a straight line from said at least one said radiation emitting device to said at least one said radiation detecting device,
   d) where said propagation path inside said animal of said radiation emitted by said radiation emitting device is just under said skin of said animal from 500 micrometers (0.5 mm) to 5 millimeters under said skin,
   e) where said propagation path of said radiation emitted by said radiation emitting device, that is propagating inside said animal, is along a direction of said propagation that makes an angle of less than 30 degrees with said skin surface SK of said animal,
   f) where said holding and containing device is formed with a re-entrant cavity between an exit window, and an entrance window,
   g) such that said radiation along said propagation path emitted by said radiation emitting device exits said holding and containing device through said exit window, to penetrate said animal, including said humans, and propagate inside a flesh of said animal, including said humans, until it reaches said entrance window, from where said radiation along said propagation path, after having propagated through said animal, enters said holding and containing device, to be detected and measured by said radiation detecting device,
   h) where, when said holding and containing device is fixed in position by said wrapping device, said flesh of said animal, including said human, is pressed to fill in a space of said re-entrant cavity existing between said exit window and said entrance window,
   i) where said re-entrant cavity includes at least part of said propagation path.

2. Said apparatus of claim 1 were said radiation is infrared radiation.

3. Said apparatus of claim 1 where said radiation is deep red radiation.

4. Said apparatus of claim 1 where said radiation is visible radiation.

5. Said apparatus of claim 1 where said radiation detecting device is capable of detecting and measuring a intensity of said radiation that propagates along said propagation path from said radiation emitting device to said radiation detecting device.

6. Said apparatus of claim 1 where said radiation detecting device is capable of detecting and measuring a intensity of said radiation that has propagated along said straight line inside said animal, from said radiation emitting device to said radiation detecting device.

7. Said apparatus of claim 1 where said surface of said holding and containing device is a flat surface while said radiation emitted by said radiation emitting device LE is positioned at a first shallow angle of inclination with said surface of said holding and containing device and with said skin of said animal, and said radiation detecting device LD is at a second shallow angle of inclination with said surface of said holding and containing device and with said skin of said animal.

8. Said apparatus of claim 1 with a collimator that rejects said radiation that propagates toward said radiation detecting device LD along directions that differ from said propagation path characteristic of each of said at least one said radiation emitting devices.

9. Said apparatus of claim 1 with a collimator that accepts into said radiation detecting device LD only said radiation that propagates toward said radiation detecting device LD along said propagation path characteristic of one of said at least one said radiation emitting devices.

10. Said apparatus of claim 1 with a collimator that rejects into said radiation detecting device LD said radiation that propagates toward said radiation detecting device LD after suffering one or more scattering events inside said flesh of said animal.

11. A method for measuring a heart beat rate of an animal, including humans, wherein said method comprises the following steps:
1) Providing a holding and containing device in fixed position with respect to a surface of a skin of said animal, including said humans, adapted to hold, contain and maintain in fixed position, a plurality of elements, where said elements are at least one from a set of said elements composed of:
   1a) at least one radiation emitting device,
   1b) at least one radiation detection device,
2) where said at least one said radiation emitting device, emits a radiation along a propagation path that is a straight line characteristic of each of said at least one said radiation emitting devices,
3) where said propagation path of said radiation emitted by said at least one said radiation emitting device is said straight line from said at least one said radiation emitting device to said at least one said radiation detection device, said propagation path being under said skin SK at a depth under said skin from 0.5 mm (500 micrometers) to 5 mm, as per FIG. 4,
4) where each of said at least one said radiation detection device is positioned so as to detect said radiation along said straight line emitted by said radiation emitting device along said propagation path characteristic of each of said at least one said radiation emitting device, while rejecting said radiation propagating along lines other than said straight line of said radiation by said radiation emitting device,
5) fixing said at least one said radiation emitting device at such locations with respect to said holding and containing device that said radiation emitted by said radiation emitting device propagates inside said animal, including said humans, along said propagation path just below said skin surface SK of said animal, located at a closest proximity to said propagation path of said radiation under said skin of said animal,
6) where said holding and containing device is formed with a re-entrant cavity between an exit window, from where said radiation along said propagation path emitted by said radiation emitting device exits said holding and containing device, to penetrate said animal, and an entrance window, from where said radiation along said propagation path, after having propagated through said animal, enters said holding and containing device, to be detected and measured by said radiation detection device, such that, when said holding and containing device is fixed in position against said skin of said animal, including said human, a flesh of said animal, including said human, is pressed to fill in a space of said re-entrant cavity existing between said exit window and said entrance window,
7) where said re-entrant cavity includes at least part of said propagation path.

12. Said method of claim 11 where said radiation emitted by said radiation emitting device is visible radiation.

13. Said method of claim 11 where said radiation emitted by said radiation emitting device is outside a range of visible radiation.

14. Said method of claim 11 where said radiation emitted by said radiation emitting device is infrared radiation.

15. Said method of claim 11 where said radiation emitted by said radiation emitting device is deep red visible radiation.

16. A method for measuring a heart beat rate of an animal, including humans, wherein said method comprises the following steps:
1) Providing a holding and containing device, in fixed position with respect to said animal, including said humans, adapted to hold, contain and maintain in fixed position with respect to a surface of a skin SK of said animal a plurality of elements, where said elements are one or more from a set of said elements composed of:
   1a) at least one radiation emitting device capable of emitting a radiation along a specific and know direction of propagation which defines a straight line,
   1b) at least one radiation detection device capable of detecting said radiation along said specific and know direction of propagation along said straight line, while rejecting said detection of said radiation that has suffered one or more scattering events inside said animal, and reaches said radiation detection devices from directions that are different than said emitted radiation along said specific and known direction of propagation along said straight line,
   1c) where said radiation detection device is capable of detecting said radiation that has propagated under said skin of said animal at depths larger than 0.5 mm (500 micrometers) and smaller than 5 mm,
   1d) at least one first or exit optical window which is capable of allowing said radiation emitted by said radiation emitting device LE to propagate from said holding and containing device into a re-entrant cavity, inside which a flesh of said animal, including said humans is pressed, 1e) at least one second or entrance optical window, which is capable of allowing said radiation that propagated along said specific and known direction of propagation to re-enter said holding and containing device to be detected by said radiation detecting device LD, 2) where each of said at least one said radiation detection device is positioned so as to detect said radiation emitted by said radiation emitting device that propagates along said specific and known direction of propagation along said straight line from said radiation emitting device, while rejecting said radiation that propagates along directions other than said specific and known direction of propagation from said radiation emitting device, 3) fixing said at least one said radiation emitting device at such locations with respect to said holding and containing device that said radiation emitted by said radiation emitting device propagates inside said animal, including said humans, at depths less than 5 mm from said surface of said skin SK of said animal, including said humans.

* * * * *